United States Patent

Okada

(10) Patent No.: US 9,924,960 B2
(45) Date of Patent: Mar. 27, 2018

(54) ENDOSCOPE TREATMENT TOOL

(71) Applicant: OLYMPUS CORPORATION, Tokyo (JP)

(72) Inventor: Tsutomu Okada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/440,004

(22) Filed: Feb. 23, 2017

(65) Prior Publication Data

US 2017/0156745 A1    Jun. 8, 2017

Related U.S. Application Data

(63) Continuation of application No. PCT/JP2016/062998, filed on Apr. 26, 2016.

(30) Foreign Application Priority Data

Jul. 1, 2015    (JP) ................................. 2015-132619

(51) Int. Cl.
*A61B 17/221*    (2006.01)
(52) U.S. Cl.
CPC .... *A61B 17/221* (2013.01); *A61B 2017/2212* (2013.01); *A61B 2017/2215* (2013.01)
(58) Field of Classification Search
CPC .......... A61B 17/221; A61B 2017/2212; A61B 2017/2215; A61B 2017/22177; A61B 2017/2217

(Continued)

(56) References Cited

U.S. PATENT DOCUMENTS 3,670,721 A * 6/1972 Fukami ................ A61B 1/0055
273/DIG. 5
4,691,705 A * 9/1987 Okada .................. A61B 17/221
606/127

(Continued)

FOREIGN PATENT DOCUMENTS

EP         2638870 A1    9/2013
JP         S57-59519 A    4/1982

(Continued)

OTHER PUBLICATIONS

International Search Report dated Jun. 21, 2016 issued in PCT/JP2016/062998.

*Primary Examiner* — Dianne Dornbusch
(74) *Attorney, Agent, or Firm* — Scully, Scott, Murphy & Presser, P.C.

(57) ABSTRACT

An endoscope treatment tool includes: a tubular sheath member insertable into a channel of an endoscope; a wire inserted into the interior of the member in such a manner that the wire can be advanced/retracted in the longitudinal direction of the member; and a distal-end treating portion provided at the distal end of the wire and made to protrude from/be pulled into a distal-end opening in the member by advancing/retracting the wire, wherein the member is configured having a two-layer structure in which a metal coil and a resin tube are layered in the radial direction and secured to each other, in the coil, lateral cross-sectional shapes of portions of a strand that are adjacent to each other in the longitudinal direction have complementary depression and protrusion that are brought into tight contact with each other, and the tube has a flexural rigidity greater than that of the coil.

8 Claims, 12 Drawing Sheets

(58) Field of Classification Search
USPC .................................................. 600/139–141
See application file for complete search history.

(56) References Cited

U.S. PATENT DOCUMENTS

| | | | | |
|---|---|---|---|---|
| 5,059,199 A * | 10/1991 | Okada | .................. | A61B 17/221 606/127 |
| 5,460,608 A * | 10/1995 | Lodin | .................. | A61M 25/005 604/103.09 |
| 5,772,578 A * | 6/1998 | Heimberger | ......... | A61B 1/0056 600/139 |
| 5,863,366 A * | 1/1999 | Snow | ............... | A61B 17/12022 156/143 |
| 5,873,866 A * | 2/1999 | Kondo | ............... | A61B 1/00071 600/140 |
| 6,015,381 A * | 1/2000 | Ouchi | .................... | A61B 10/06 600/104 |
| 6,083,152 A * | 7/2000 | Strong | ................. | A61B 1/0055 600/121 |
| 6,443,909 B1 * | 9/2002 | Ouchi | .................... | A61B 10/06 600/562 |
| 7,060,150 B2 * | 6/2006 | Banas | ...................... | A61F 2/06 156/184 |
| 7,850,678 B2 * | 12/2010 | Toyama | ............. | A61B 1/00071 600/101 |
| 7,905,877 B1 * | 3/2011 | Jimenez | ............ | A61M 25/0012 604/523 |
| 7,955,340 B2 * | 6/2011 | Michlitsch | ......... | A61B 1/00135 600/104 |
| 8,047,236 B2 * | 11/2011 | Perry | ................... | A61B 1/0055 135/155 |
| 8,075,474 B2 * | 12/2011 | Honda | ............... | A61B 1/00133 600/104 |
| 8,100,031 B2 * | 1/2012 | Zubiate | ...................... | B25J 9/06 600/140 |
| 8,221,390 B2 * | 7/2012 | Pal | ............................ | A61F 2/95 604/535 |
| 8,262,563 B2 * | 9/2012 | Bakos | .................... | A61B 1/005 600/114 |
| 8,591,404 B2 * | 11/2013 | Yamazaki | ............ | A61B 1/0057 600/139 |
| 8,702,595 B2 * | 4/2014 | Ueki | .................... | A61B 1/0052 600/144 |
| 9,192,499 B2 * | 11/2015 | Gibbons, Jr. | ........... | A61F 2/966 |
| 9,375,257 B2 * | 6/2016 | Suzuki | ............... | A61B 18/1445 |
| 2002/0032369 A1 * | 3/2002 | Takase | ............... | A61B 1/00071 600/140 |
| 2004/0242966 A1 * | 12/2004 | Barry | .................... | A61B 1/0055 600/146 |
| 2006/0178560 A1 * | 8/2006 | Saadat | ................. | A61B 1/0055 600/114 |
| 2007/0100285 A1 * | 5/2007 | Griffin | .............. | A61M 25/0013 604/164.11 |
| 2008/0009831 A1 * | 1/2008 | Griffin | ................ | A61M 25/005 604/531 |
| 2008/0172037 A1 * | 7/2008 | Huang | ............ | A61M 25/0043 604/526 |
| 2010/0057051 A1 * | 3/2010 | Howat | .................. | A61M 25/00 604/526 |
| 2010/0228150 A1 * | 9/2010 | Zimmerman | ......... | A61M 25/09 600/585 |
| 2012/0053415 A1 * | 3/2012 | Bunch | .................. | A61B 1/0055 600/121 |
| 2012/0101562 A1 * | 4/2012 | Gunderson | ............. | A61F 2/966 623/1.12 |
| 2014/0012283 A1 | 1/2014 | Yasuda et al. | | |

FOREIGN PATENT DOCUMENTS

| | | |
|---|---|---|
| JP | S59-231286 A | 12/1984 |
| JP | S62-14812 Y2 | 4/1987 |
| JP | H08-131550 A | 5/1996 |
| JP | 2002-224023 A | 8/2002 |
| JP | 2006-314715 A | 11/2006 |
| JP | 2007-307070 A | 11/2007 |
| JP | 5226906 B1 | 7/2013 |
| WO | WO 2012/141213 A1 | 10/2012 |

* cited by examiner

ENDOSCOPE TREATMENT TOOL

CROSS-REFERENCE TO RELATED APPLICATIONS

This is a continuation of International Application PCT/JP2016/062998 which is hereby incorporated by reference herein in its entirety.

This application is based on Japanese Patent Application No. 2015-132619, the contents of which are incorporated herein by reference.

TECHNICAL FIELD

The present invention relates to an endoscope treatment tool.

BACKGROUND ART

In the related art, as a means of removing a large calculus that has grown in the bile duct from the bile duct, there is a known calculus-crushing treatment tool with which a calculus is crushed by using a basket formed of wires (for example, see Patent Literature 1).

With this treatment tool, the basket in which the calculus is captured is pulled into a sheath from a distal-end opening in the sheath, the basket is contracted, and thus, the calculus is crushed by squeezing the calculus by contracting the basket.

In the calculus-crushing treatment tool, because the compression force exerted on the sheath when crushing the calculus is high, in Patent Literature 1, a coil sheath having excellent compression resistance is used. Also, a resin inner cylinder is disposed on the inner side of the coil sheath in order to reduce the friction due to irregularities on the inner surface of the coil sheath, and thus, a smooth motion of the basket is ensured.

In the case in which the lateral cross-section of the strand constituting the coil sheath has a circular shape, there is a risk of portions of the strand buckling by shifting in radial directions of the coil sheath with respect to each other when the compression force is increased. If the strand diameter and the coil-sheath diameter are increased in order to avoid this risk, the flexural rigidities thereof are increased, which makes the work involved in inserting the coil sheath into the bile duct from the duodenal papilla difficult.

As a buckle-resistant coil sheath, there is a known coil sheath in which the strand has a lateral cross-section having depressions and protrusions, and in which adjacent portions of the strand are brought into contact with each other by means of surface contact between the depressions and the protrusions (for example, see Patent Literature 2).

With this coil sheath, as compared with the coil sheath having a circular lateral cross-section, buckling is suppressed by means of the friction due to surface contact between the relevant portions of the strand. Therefore, it is possible to maintain the compression resistance thereof even if the width of the coil sheath is reduced in the radial direction.

CITATION LIST

Patent Literature

{PTL 1} Japanese Examined Utility Model Application, Publication No. Sho62-14812

{PTL 2} Japanese Unexamined Patent Application, Publication No. Sho57-59519

SUMMARY OF INVENTION

Solution to Problem

An aspect of the present invention is an endoscope treatment tool including: a tubular sheath member that can be inserted into a channel of an endoscope; a wire that is inserted into an interior of the sheath member in such a manner that the wire can be advanced/retracted in a longitudinal direction of the sheath member; and a distal-end treating portion that is provided at a distal end of the wire and that is made to protrude from/be pulled into a distal-end opening in the sheath member by advancing/retracting the wire, wherein the sheath member is configured having a two-layer structure in which a metal coil and a resin tube are layered in a radial direction and secured to each other at least at both ends in the longitudinal direction thereof, in the metal coil, lateral cross-sectional shapes of portions of a strand that are adjacent to each other in the longitudinal direction have a complementary depression and protrusion that are brought into tight contact with each other, and the resin tube has a flexural rigidity that is greater than that of the metal coil.

DESCRIPTION OF EMBODIMENT

An endoscope treatment tool 1 according to an embodiment of the present invention will be described below with reference to the drawings.

Figure 1:
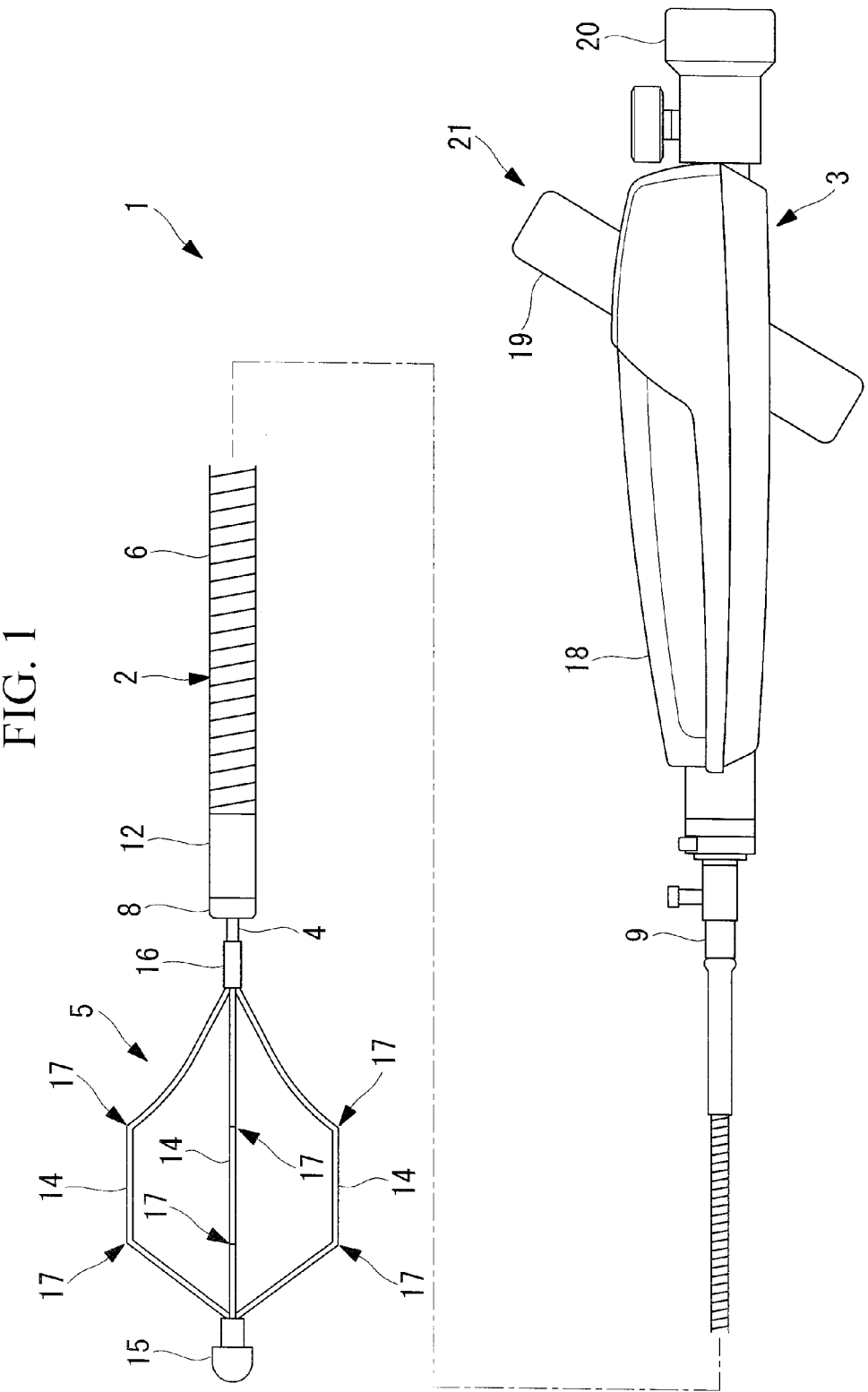
FIG. 1 is a diagram showing the overall configuration of an endoscope treatment tool according to an embodiment of the present invention.

The endoscope treatment tool 1 according to this embodiment is a treatment tool for collecting or crushing a calculus X in a bile duct B, and is provided with, as shown in FIG. 1: an elongated tubular sheath member 2 that can be inserted into a channel of an endoscope 30 (see FIG. 4); a manipulating portion 3 that is secured on the proximal-end side of the sheath member 2 and that is manipulated by an operator outside the body; a manipulating wire (wire) 4 that is advanced/retracted in the longitudinal direction of the sheath member 2 inside the sheath member 2 by means of manipulation performed at the manipulating portion 3; and a basket portion (distal-end treating portion) 5 that is provided at the distal end of the manipulating wire 4 and that is made to protrude from/be pulled into a distal-end opening in the sheath member 2 by advancing/retracting the manipulating wire 4.

Figure 2:
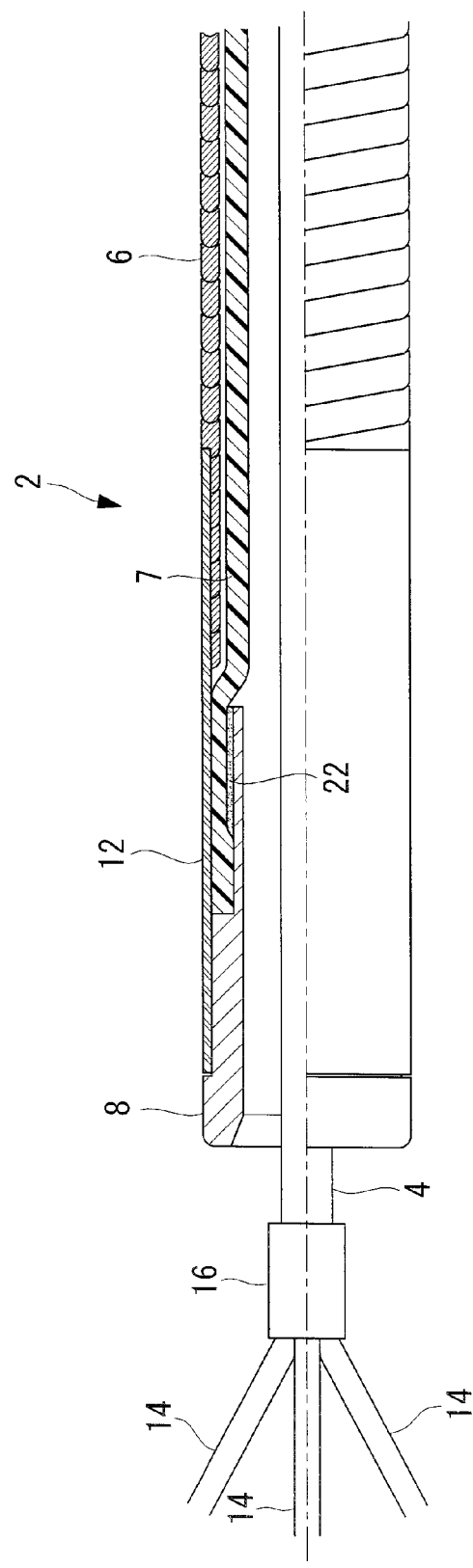
FIG. 2 is a partially cutaway magnified view showing a distal-end portion of a sheath member of the endoscope treatment tool in FIG. 1.
Figure 3:
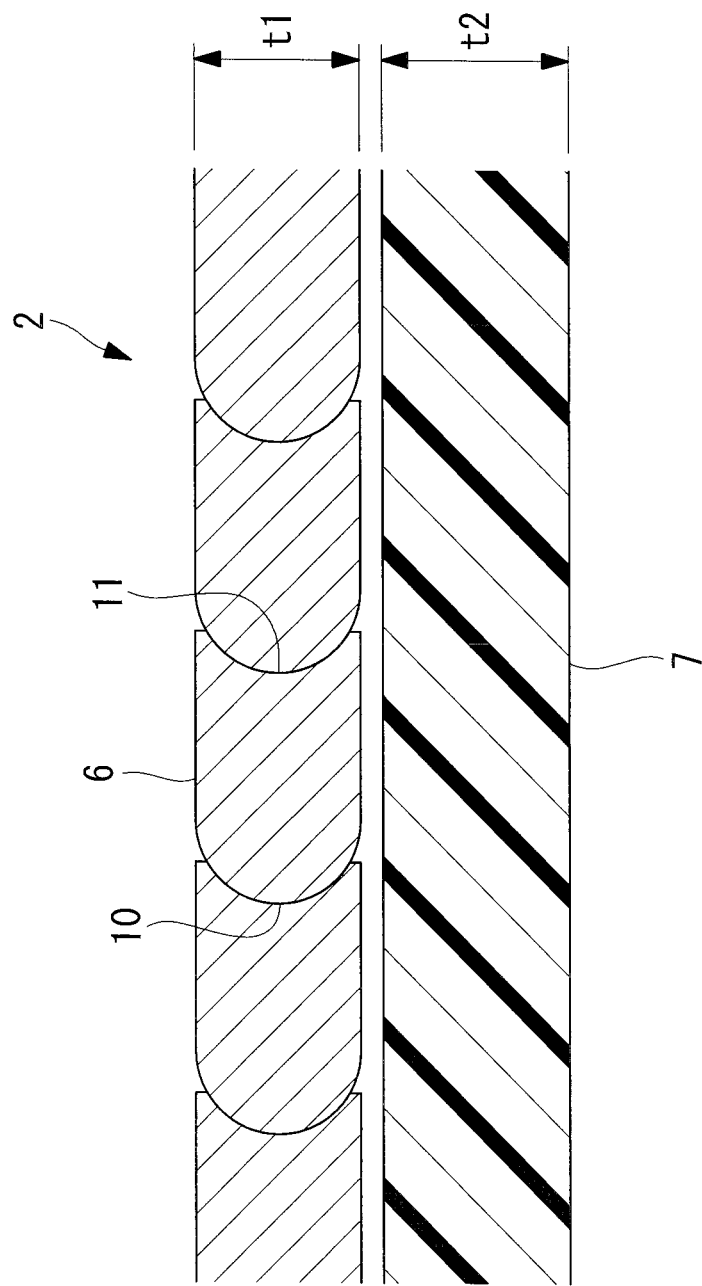
FIG. 3 is a longitudinal sectional view showing, in a magnified view, the structure of the sheath member of the endoscope treatment tool in FIG. 1.

As shown in FIG. 2, the sheath member 2 is provided with: a metal coil 6; a resin tube 7 that is inserted into the metal coil 6; a cylindrical distal-end member 8 that secures these components at distal ends thereof; and a proximal-end member 9 that secures these components at proximal ends thereof. As shown in FIG. 3, the metal coil 6 is formed by winding a band-plate-like metal strand into a tightly coiled shape.

As shown in FIG. 3, the lateral cross-section of the strand is formed so as to have a constant rectangular shape, which has, on one edge, an arc-shaped protrusion 10 and, on the other edge, an arc-shaped depression 11 that is complementary to the protrusion 10. By doing so, when the strand is wound into the tightly coiled shape, the depression 11 is disposed in tight contact with the protrusion 10 of an adjacent portion of the strand on one side, and the protrusion 10 is disposed in tight contact with the depression 11 of an adjacent portion of the strand on the other side.

With the metal coil 6 in which the depressions 11 and the protrusions 10 of the adjacent portions of the strand are in tight contact with each other, as compared with a metal coil in the related art, which has a circular lateral cross-section, by bringing the adjacent portions of the strand into surface contact with each other, the friction between them is increased, thus achieving a high enough compression resistance to prevent buckling even when a large compression force acts thereon.

In this embodiment, within a range in which a required compression resistance can be achieved, the outer diameter of the metal coil 6 and also the thickness thereof in the radial direction are reduced as much as possible. As a result, the metal coil 6 alone has a flexural rigidity so low that the shape thereof cannot be maintained by itself when an external force acts thereon in a direction that intersects the longitudinal direction thereof.

The resin tube 7 is formed of, for example, a fluorine-based resin. The resin tube 7 is inserted into the inner circumferential side of the metal coil 6, thus facilitating advancing/retracting of the manipulating wire 4 and the basket portion 5 by reducing the friction between the metal coil 6 and the manipulating wire 4 and the basket portion 5 that are disposed on the inner side of the resin tube 7.

In addition, with the resin tube 7, the thickness thereof in the radial direction is set to be greater than that of the metal coil 6, and the relationship described below holds:

$$t2 > t1,$$

where t1 is the thickness of the metal coil 6 in the radial direction, and t2 is the thickness of the resin tube 7 in the radial direction.

Also, the resin tube 7 has a flexural rigidity that is greater than that of the metal coil 6.

In addition, as shown in FIG. 2, the distal-end member 8 is formed in a cylindrical shape, the distal end of the resin tube 7 is secured thereto, and the metal coil 6 is joined therewith via a cover member 12 by means of brazing or the like. Reference sign 22 indicates an adhesive member that is filled in a gap between the distal-end member 8 and the resin tube 7.

In addition, the proximal-end member 9 is also formed in a cylindrical shape, the proximal end of the metal coil 6 is joined therewith by means of brazing or the like, and the resin tube 7 is secured thereto by using an adhesive. By doing so, the sheath member 2 has a structure in which the distal end of a tubular member having a two-layer structure formed of the metal coil 6 and the resin tube 7 is secured by the distal-end member 8, and the proximal end thereof is secured by the proximal-end member 9.

As shown in FIG. 1, the basket portion 5 is provided with a plurality of elastic wires 14, and the plurality of elastic wires 14 are bound into a single bundle by a distal-end tip 15 at the distal ends thereof, and are secured to the distal end of the manipulating wire 4 at the proximal ends thereof in a state in which the elastic wires 14 are bundled by a linkage member 16. The individual elastic wires 14 are provided with a plurality of flexing portions 17 between the distal-end tip 15 and the linkage member 16. By doing so, the basket portion 5 is configured so as to expand into a basket shape in a free state in which no external force is exerted thereon.

In addition, by retracting the manipulating wire 4 into the sheath member 2, the basket portion 5 is pulled into the sheath member 2, while being contracted by folding the flexing portions 17, so as to leave the distal-end tip 15 at the exterior thereof. By doing so, it is possible to collect a calculus, for example, a gallstone or the like, that is accommodated among the plurality of elastic wires 14, which constitute the basket portion 5, by squeezing the calculus with the contracted basket portion 5, thus maintaining the captured state, or it is possible to crush the calculus by compressing it by more strongly squeezing them.

The manipulating portion 3 is provided with: a main unit 18 that secures the proximal-end member 9 of the sheath member 2 in an attachable/detachable manner; a gripping portion 20 to which the proximal-end portion of the manipulating wire 4 that has passed through a through-hole formed in the main unit 18 is secured in an attachable/detachable manner; and a pulling mechanism 21 that is provided in the main unit 18 and that is used to pull in the gripping portion 20 toward the proximal-end side with respect to the main unit 18. The pulling mechanism 21 is provided with a handle 19 that is rotated by the operator, and a rack-and-pinion mechanism (not shown) that converts the rotation of the handle 19 into the linear movement of the gripping portion 20 toward the proximal-end side. The detailed structure of the manipulating portion 3 is the same as that disclosed in, for example, Japanese Unexamined Patent Application, Publication No. 2006-314715.

The operation of the thus-configured endoscope treatment tool 1 according to this embodiment will be described below.

An example in which the calculus X in, for example, the bile duct B is collected or crushed by using the endoscope treatment tool 1 according to this embodiment will be described. Note that, although collection or crushing of the calculus X formed in the bile duct B will be described as an example, the treatment target site is not limited to the bile duct B.

Figure 4:
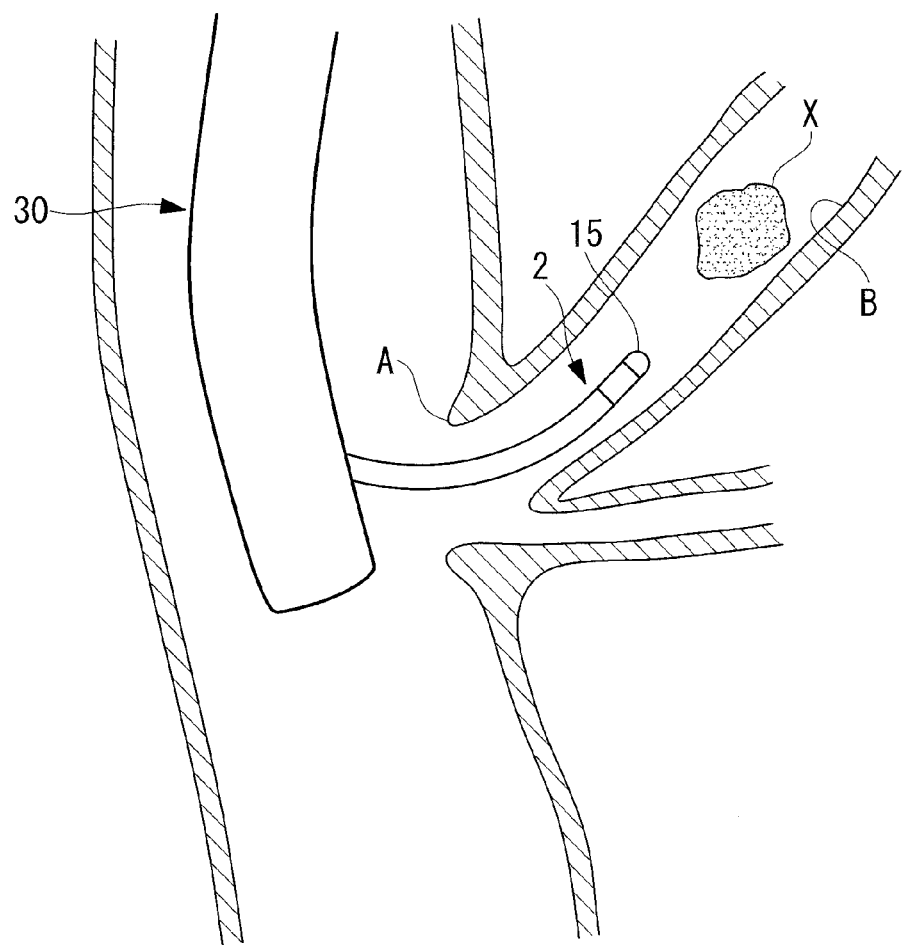
FIG. 4 is a diagram showing a state in which the sheath member of the endoscope treatment tool in FIG. 1 is inserted into the bile duct from the papilla.

As shown in FIG. 4, when collecting or crushing the calculus X in the bile duct B, the endoscope treatment tool 1 is inserted into the bile duct B from a duodenum papilla A in the state in which the basket portion 5 is accommodated inside the sheath member 2 via the channel whose opening is provided in a side surface at the distal-end portion of the endoscope 30 inserted into the duodenum.

In this case, in this embodiment, because the thickness t1 of the metal coil 6 in the radial direction is reduced and the outer diameter thereof is set to be small, the diameter of the sheath member 2 is reduced, and thus, it is possible to use a thin endoscope 30 having a small-diameter channel and it is also possible to easily insert the endoscope 30 into the narrow bile duct B.

In addition, because the flexural rigidity of the metal coil 6 is set to be lower than the flexural rigidity of the resin tube 7 by configuring the metal coil 6 so as to have low thickness and diameter, the sheath member 2 has a high flexibility and is easily bent, and thus, it is possible to easily insert the sheath member 2 into the bile duct B.

Figure 5:
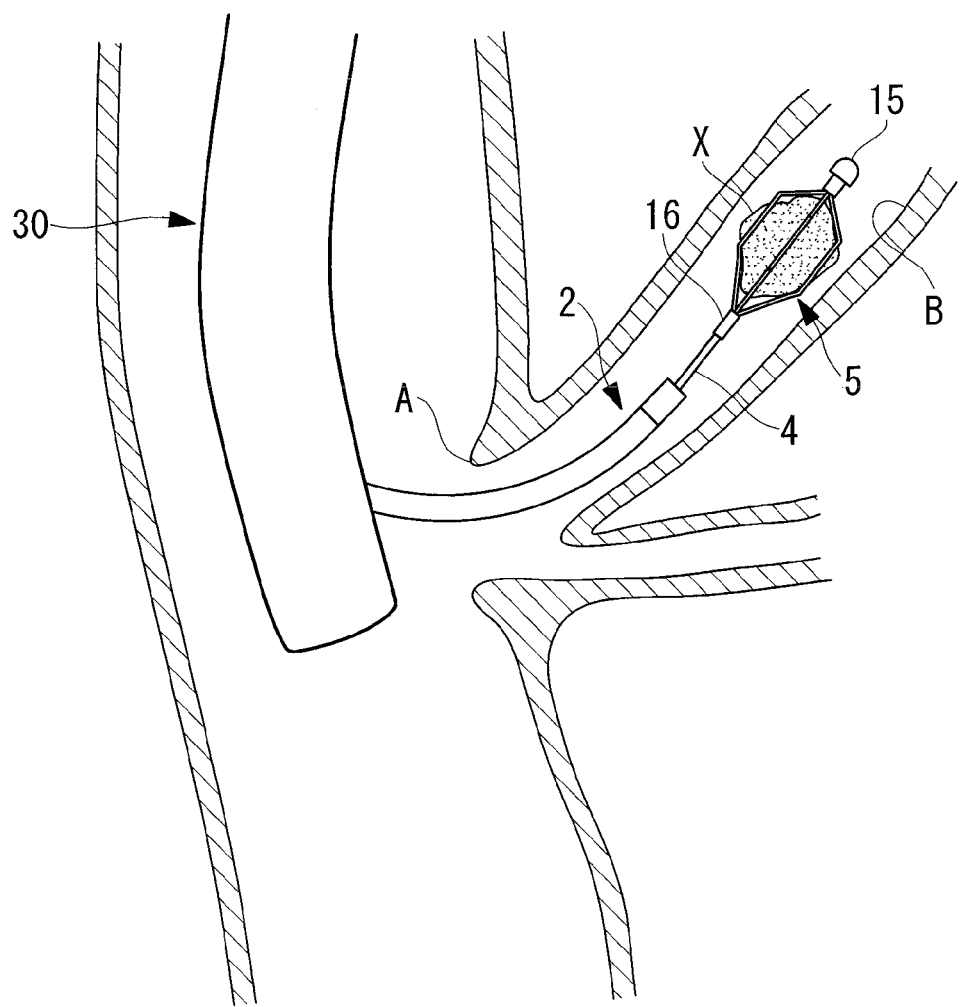
FIG. 5 is a diagram showing a state in which a calculus is captured by making a basket portion protrude starting from the state in FIG. 4.

After the insertion into the bile duct B, by advancing the gripping portion 20 with respect to the main unit 18, the manipulating wire 4, which is secured to the gripping portion 20, is advanced, as shown in FIG. 5, the basket portion 5 is made to protrude from the distal-end opening in the sheath member 2, the folded elastic wires 14 are unfolded, and thus, the basket portion 5 is expanded. In this state, the basket portion 5 is advanced/retracted and rotated in the bile duct B, and the calculus X in the bile duct B is taken into the basket portion 5.

Subsequently, by retracting the gripping portion 20 with respect to the main unit 18, the manipulating wire 4 is pulled back, a portion of the basket portion 5 is pulled into the sheath member 2, the basket portion 5 is folded, and thus, the calculus X is squeezed by the elastic wires 14. When the calculus X is small, it is possible to recover the calculus X by maintaining the calculus X in a captured state by using the folded basket portion 5 and by pulling the calculus X into the channel of the endoscope 30.

When the calculus X is large, it is possible to crush the calculus X by pulling the manipulating wire 4 toward the proximal-end side by rotating the handle 19, thus generating a high tensile force in the elastic wires 14.

In this case, when crushing the calculus X, because the manipulating wire 4 is strongly pulled in a state in which the calculus X abuts the distal-end member 8 of the sheath member 2, a large compression force is exerted on the sheath member 2.

With this embodiment, because the compression force is received by the metal coil 6 in which the adjacent portions of the strand are in surface contact with each other, there is an advantage in that it is possible to exert high tensile forces on the elastic wires 14 without causing the sheath member 2 to buckle even if the thickness t1 in the radial direction is small and the outer diameter thereof is small.

In addition, with the endoscope treatment tool 1 according to this embodiment, because the sheath member 2 is provided, which has a high enough compression resistance to endure the compression force for crushing calculus while maintaining a small outer diameter and a high flexibility, it is also possible to crush a large calculus X while maintaining good insertability of the calculus-collecting endoscope treatment tool 1. Therefore, there is an advantage in that it is not necessary to exchange the endoscope treatment tool 1 or the endoscope 30 during operation, and that it is possible to considerably reduce the burden on the patient.

Figure 6:
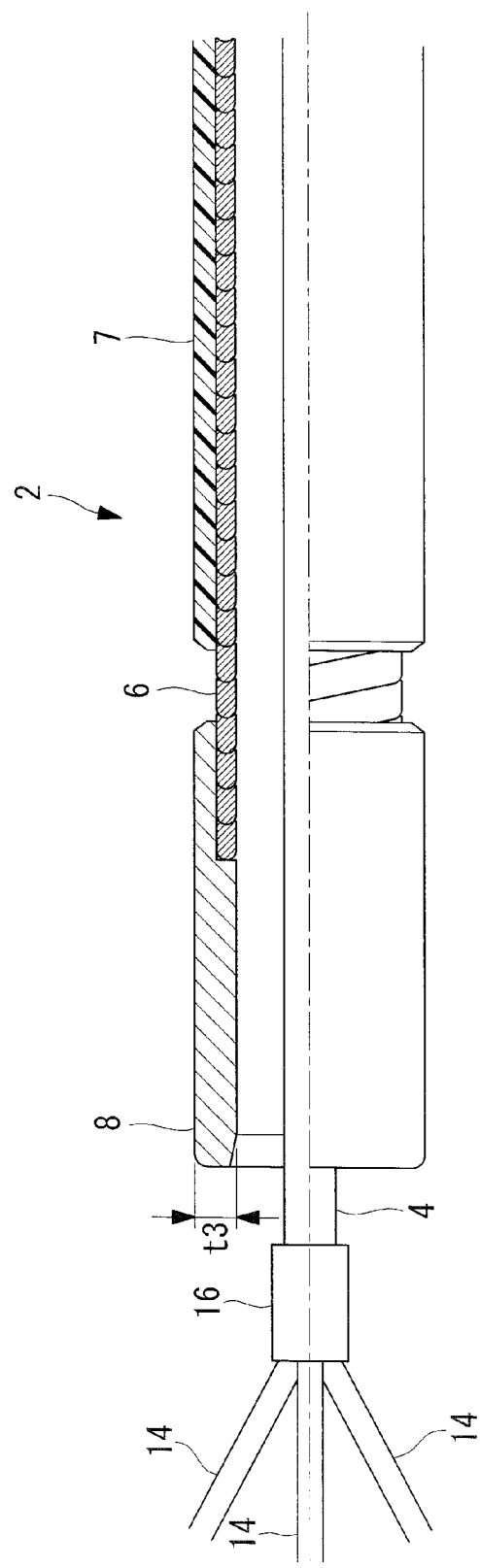
FIG. 6 is a partially cutaway magnified view showing a distal-end portion of a sheath member of a modification of the endoscope treatment tool in FIG. 1.
Figure 7:
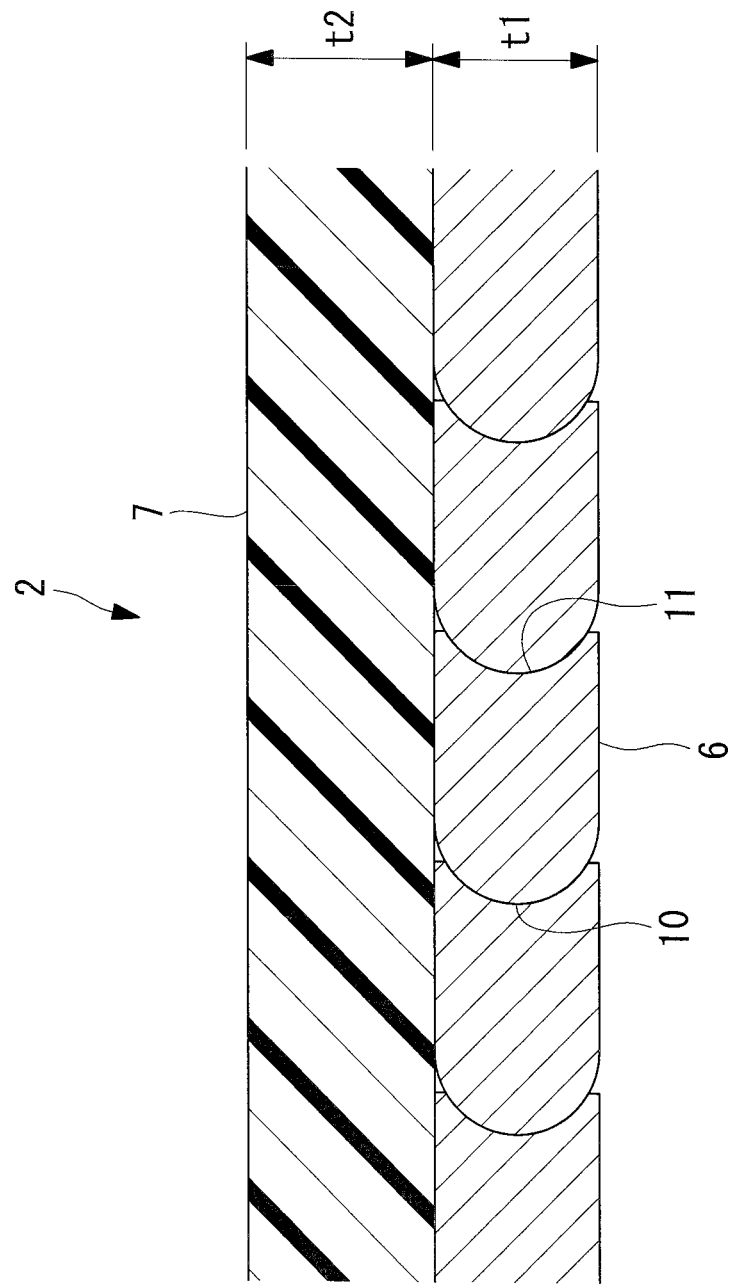
FIG. 7 is a longitudinal sectional view showing, in a magnified view, the structure of the sheath member of the endoscope treatment tool in FIG. 6.

Note that, in this embodiment, although the sheath member 2 has the resin tube 7 disposed on the inner circumferential side of the metal coil 6, alternatively, as shown in FIGS. 6 and 7, the resin tube 7 may be disposed on the outer circumferential side of the metal coil 6. By doing so, by causing the resin tube 7 disposed on the outer circumferential side of the metal coil 6 to thermally contract, it is possible to secure the resin tube 7 and the metal coil 6 with each other by bringing the resin tube 7 into tight contact with the outer circumferential surface of the metal coil 6 over the entire length thereof.

By doing so, it is possible to prevent a gap from forming between the metal coil 6 and the resin tube 7, and thus, it is possible to further reduce the outer diameter of the sheath member 2. In addition, by disposing the resin tube 7 on the outer circumferential side of the metal coil 6, it is possible to increase the outer diameter of the resin tube 7 as compared with the case in which the resin tube 7 is disposed on the inner circumferential side, and thus, it is possible to maintain the flexural rigidity even if the thickness t1 in the radial direction is reduced. As a result, it is possible to reduce the diameter of the sheath member 2 while maintaining the flexural rigidity.

In this case, it is preferable that the inner diameter of the distal-end member 8 be the same as the inner diameter of the metal coil 6, and that the thickness of the distal-end member 8 in the radial direction satisfy relational expression (1) described below:

$$t3 > t1 + t2 \qquad (1),$$

where t3 is the thickness of the distal-end member 8 in the radial direction.

By doing so, the distal-end member 8, which is disposed on the distal-end side of the resin tube 7, has an outer diameter that is one size greater than the outer diameter of the resin tube 7, and thus, there is an advantage in that it is possible to protect the distal end of the resin tube 7 by using the distal-end member 8 so that the distal end of the resin tube 7 is not separated from the metal coil 6 during insertion.

Figure 8:
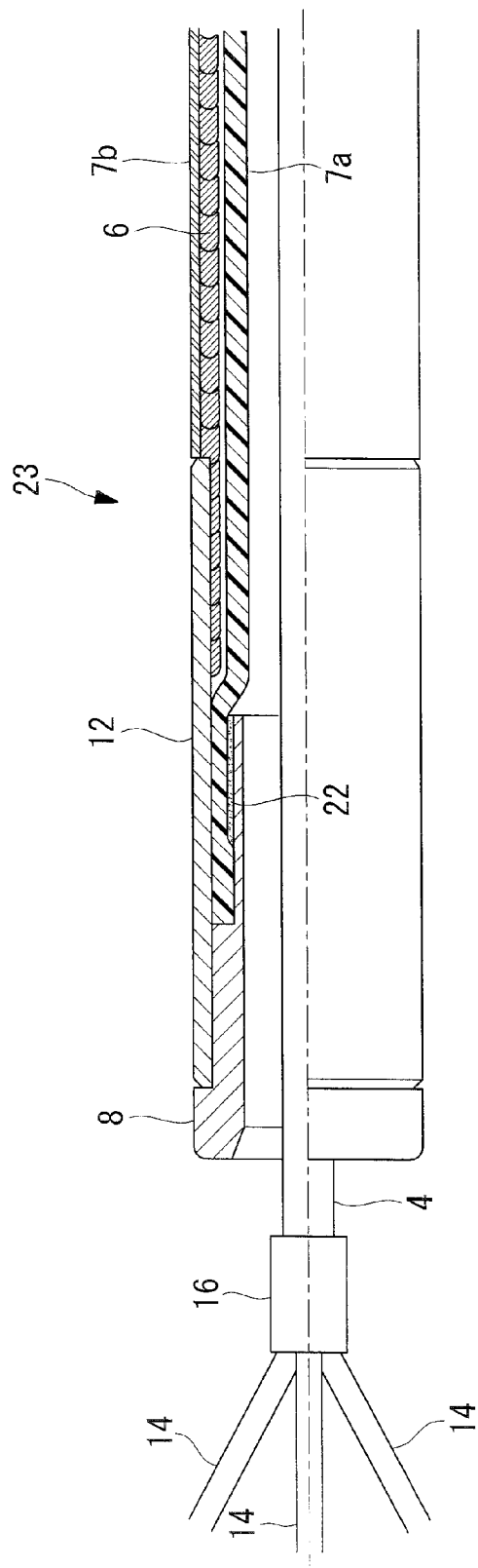
FIG. 8 is a partially cutaway magnified view showing a distal-end portion of a sheath member of another modification of the endoscope treatment tool in FIG. 1.
Figure 9:
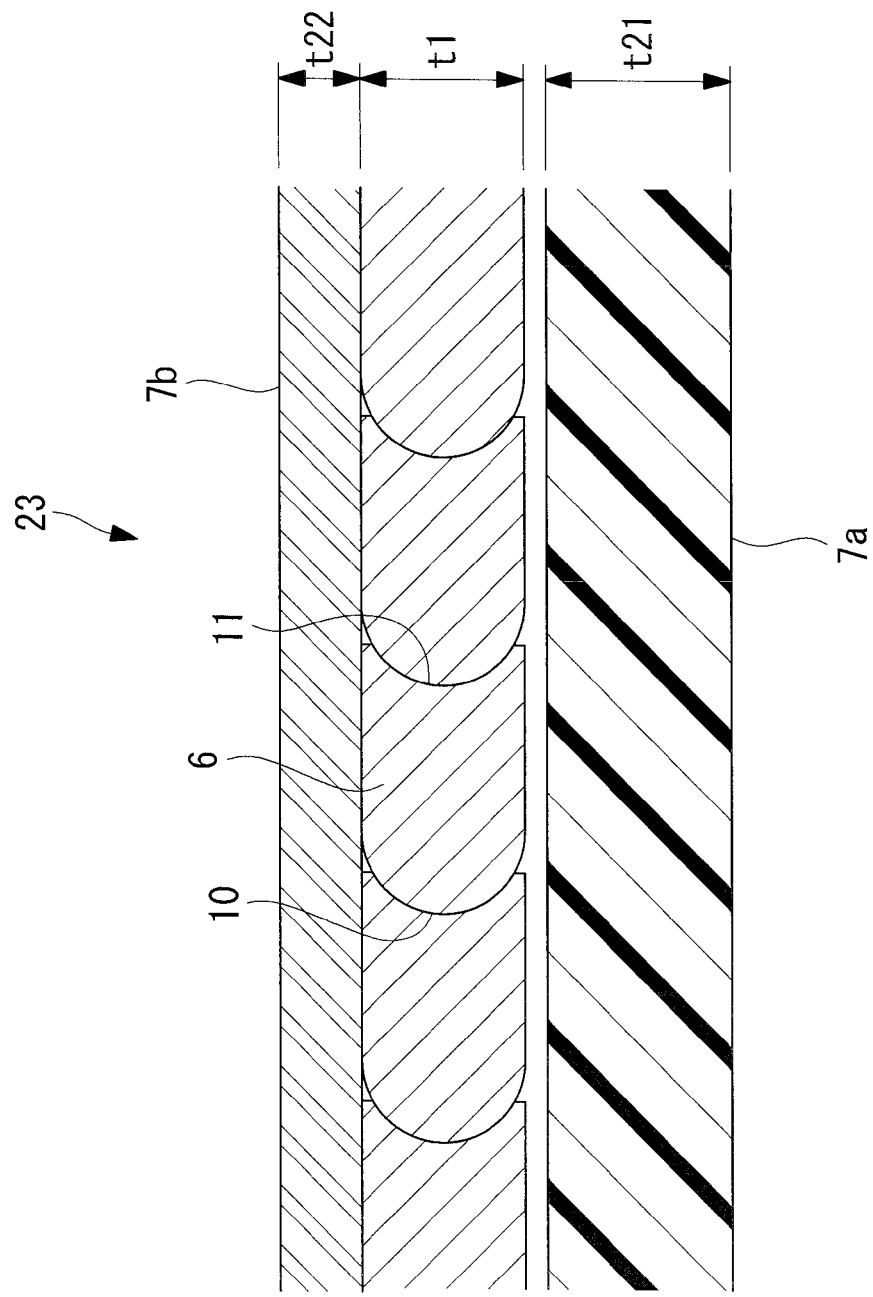
FIG. 9 is a longitudinal sectional view showing, in a magnified view, the structure of the sheath member of the endoscope treatment tool in FIG. 8.

In addition, as shown in FIGS. 8 and 9, it is permissible to employ a sheath member 23 having a three-layer structure in which resin tubes 7a and 7b are disposed on the inner circumferential side and the outer circumferential side of the metal coil 6, respectively. In this case, the thickness t1 of the metal coil 6 in the radial direction is made smaller than t2, which is the sum of thicknesses t21 and t22 of the two resin tubes 7 in the radial direction. Thus, in this case also, it is preferable that the above-described expression (1) be satisfied.

Figure 10:
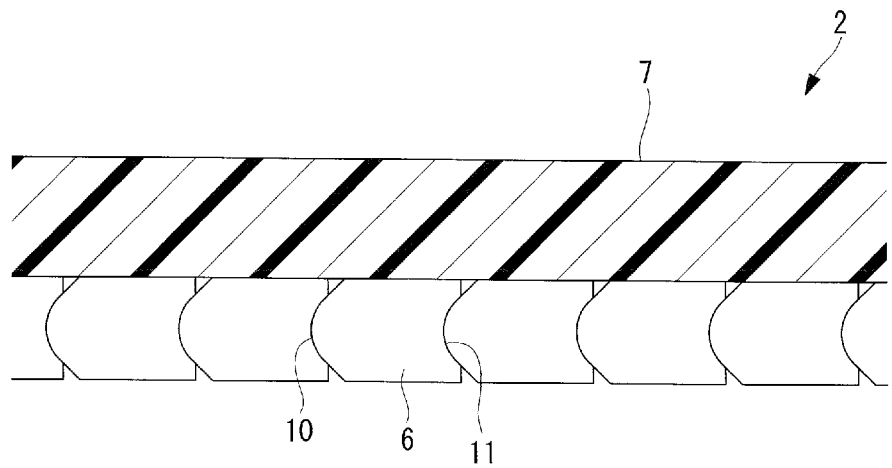
FIG. 10 is a longitudinal sectional view showing, in a magnified view, the structure of a sheath member of another modification of the endoscope treatment tool in FIG. 1.

In addition, although a strand in which the protrusion 10 on one edge thereof and the depression 11 on the other edge thereof are arc shaped is employed as the strand of the metal coil 6 in this embodiment, the shape thereof is not limited thereto. For example, as shown in FIG. 10, a protrusion 10 in which the center portion of the strand in the radial direction is partially arc shaped may be employed as the protrusion 10.

Figure 11:
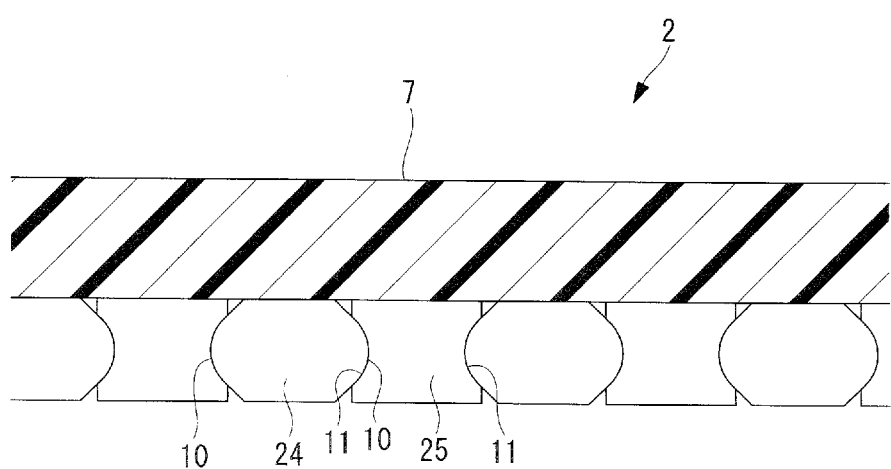
FIG. 11 is a longitudinal sectional view showing, in a magnified view, the structure of a sheath member of another modification of the endoscope treatment tool in FIG. 1.

In addition, as shown in FIG. 11, the metal coil 6 may be a multithread coil in which a first strand 24 having the protrusions 10 on both edges thereof and a second strand 25 having the depressions 11 on both edges thereof are wound in an alternating manner.

Figure 12:
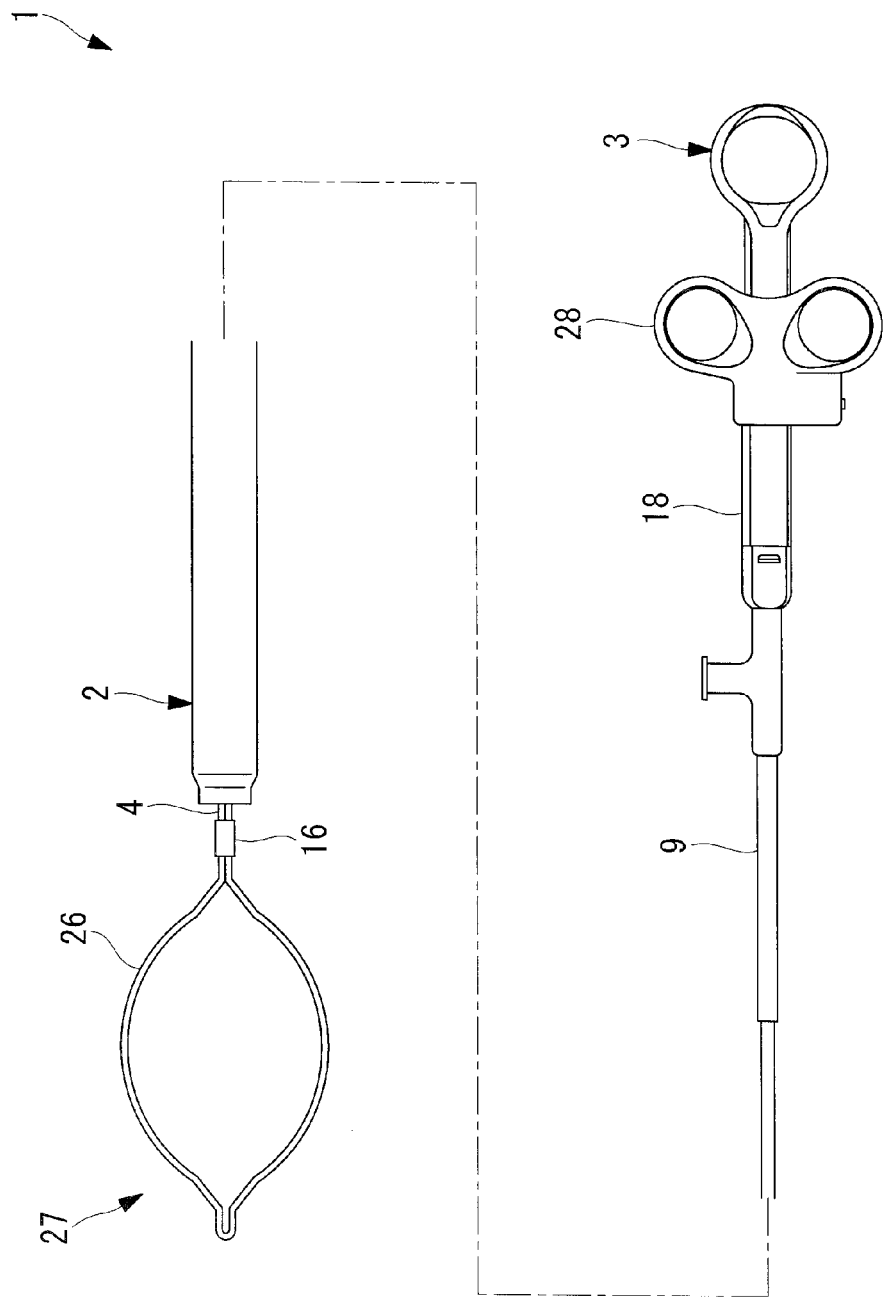
FIG. 12 is a longitudinal sectional view showing the overall configuration of another modification of the endoscope treatment tool in FIG. 1.

In addition, in this embodiment, although the basket portion 5 in which the plurality of elastic wires 14 are bundled into a basket shape is employed as the distal-end treating portion, alternatively, as shown in FIG. 12, a high-frequency snare 27 formed of a loop-shaped metal wire 26 may be employed.

In this case, when the operator pulls a slider 28 in the axial direction with respect to the main unit 18, the diameter of the loop of the metal wire 26 is reduced, thus snaring the treatment site.

Figure 13:
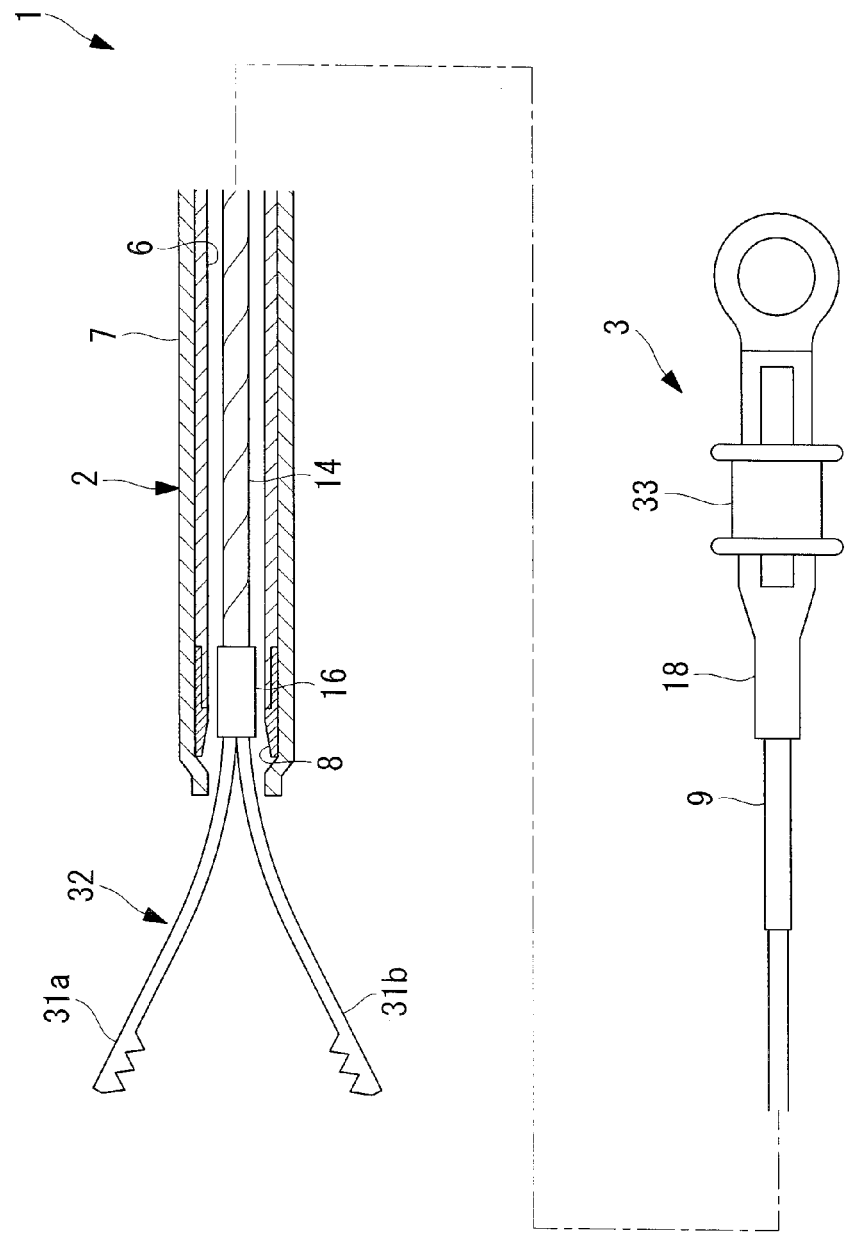
FIG. 13 is a longitudinal sectional view showing the overall configuration of another modification of the endoscope treatment tool in FIG. 1.

In addition, as shown in FIG. 13, gripping forceps 32 provided with a pair of forceps pieces 31a and 31b may be employed as the distal-end treating portion.

In this case, when the operator pulls a slider 33 in the axial direction with respect to the main unit 18, the forceps pieces 31a and 31b are closed, thus gripping the treatment site.

The above-described embodiment leads to the following inventions.

An aspect of the present invention is an endoscope treatment tool including: a tubular sheath member that can be inserted into a channel of an endoscope; a wire that is inserted into an interior of the sheath member in such a manner that the wire can be advanced/retracted in a longitudinal direction of the sheath member; and a distal-end treating portion that is provided at a distal end of the wire and that is made to protrude from/be pulled into a distal-end opening in the sheath member by advancing/retracting the wire, wherein the sheath member is configured having a two-layer structure in which a metal coil and a resin tube are layered in a radial direction and secured to each other at least at both ends in the longitudinal direction thereof, in the metal coil, lateral cross-sectional shapes of portions of a strand that are adjacent to each other in the longitudinal direction have a complementary depression and protrusion that are brought into tight contact with each other, and the resin tube has a flexural rigidity that is greater than that of the metal coil.

With this aspect, the tubular sheath member in which the distal-end treating portion is accommodated is inserted into the body via the channel of the endoscope inserted into the body of a patient, the wire is advanced with respect to the sheath member in a state in which the distal end of the sheath member has reached an affected site, and thus, the distal-end treating portion provided at the distal end of the wire is made to protrude from the distal-end opening in the sheath member. A compression force acts on the sheath member due to the tensile force in the wire when the distal-end treating portion is pulled into the sheath member by retracting the wire into the sheath member after treating the affected site by using the distal-end treating portion that is made to protrude from the distal-end opening in the sheath member.

Because the complementary depression and protrusion of adjacent portions of the strand are brought into tight contact with each other in the metal coil constituting the sheath member, the compression force exerted on the metal coil is supported by the surface contact between adjacent portions of the strand. By doing so, buckling of the sheath member is prevented by the friction between the contact surfaces between adjacent portions of the strand in the metal coil even if a high compression force acts on the sheath member.

In this case, when the outer diameter of the metal coil is reduced and the thickness thereof in the radial direction is reduced within a range in which a required compression resistance can be maintained, the flexural rigidity of the metal coil is significantly reduced, and thus, it becomes impossible to keep the shape thereof solely by means of the metal coil. With this aspect, because the resin tube, which is layered on the metal coil in the radial direction, thus forming the two-layer structure of the sheath member together with the metal coil, has a flexural rigidity that is greater than that of the metal coil, it is possible to maintain a required flexural rigidity in the sheath member by means of the flexural rigidity of the resin tube.

In other words, with this aspect, because a high compression resistance is maintained by the metal coil, and the required flexural rigidity is maintained by the resin tube, it is possible to reduce the diameter of the sheath member by reducing the thickness of the metal coil in the radial direction. In addition, because the flexural rigidity is maintained by the resin tube, it is possible to provide an endoscope treatment tool that is easy to bend and has good insertability.

In the above-described aspect, the distal-end treating portion may be a basket portion in which a plurality of elastic wires are bundled into a basket shape, that is expanded in a state in which the basket portion is made to protrude from the sheath member, and that is contracted by being pulled into the sheath member.

By doing so, because the basket portion with which a calculus is crushed is accommodated in a contracted state, it is possible to reduce the diameter of the sheath member.

In the above-described aspect, the strand of the metal coil may have a lateral cross-sectional shape in which the protrusion on one side in the longitudinal direction is arc shaped and the depression on the other side thereof is arc shaped.

By doing so, it is possible to provide an endoscope treatment tool that is easy to bend and has good insertability by achieving a high compression resistance and a low flexural rigidity by means of a single metal coil and by maintaining the flexural rigidity by means of the resin tube.

In addition, in the above-described aspect, the resin tube may be disposed on an inner circumferential side of the metal coil.

By doing so, it is possible to reduce, by using the resin tube for maintaining the flexural rigidity, sliding resistances of the wire and the distal-end treating portion that are advanced/retracted in the interior of the sheath member.

In addition, in the above-described aspect, a thickness of the metal coil in a radial direction and a thickness of the resin tube in a radial direction may have a relationship described below:

$$t1 < t2,$$

where t1 is the thickness of the metal coil in the radial direction, and t2 is the thickness of the resin tube in the radial direction.

In addition, in the above-described aspect, the resin tube may be disposed on an outer circumferential side of the metal coil.

By doing so, it is possible to dispose the resin tube at an outer surface of the metal coil in tight contact therewith over the entire length thereof by causing thermal contraction of the resin tube. By doing so, it is possible to further reduce the outer diameter of the sheath member by eliminating the gap between the resin tube and the metal coil in the radial direction. In addition, by disposing the resin tube on the outer circumferential side, it is possible to achieve the same flexural rigidity even if the thickness in the radial direction is reduced. Therefore, it is possible to further reduce the outer diameter of the sheath member as compared with the case in which the resin tube is disposed on the inner circumferential side.

In addition, in the above-described aspect, the sheath member may be provided with, at a distal end thereof in the longitudinal direction, a cylindrical distal-end member that secures at least the metal coil and that has substantially the same inner diameter as that of the metal coil; and a thickness of the metal coil in a radial direction, a thickness of the resin tube in a radial direction, and a thickness of the distal-end member in a radial direction may have a relationship described below:

$$t3 > t1 + t2,$$

where t1 is the thickness of the metal coil in the radial direction, t2 is the thickness of the resin tube in the radial direction, and t3 is the thickness of the distal-end member in the radial direction.

By doing so, the metal coil and the resin tube are disposed within the thickness range of the distal-end member in the radial direction, the resin tube does not protrude radially outward from the distal-end member, and thus, it is possible to make it less likely for the distal-end portion of the resin tube to be separated from the metal coil.

REFERENCE SIGNS LIST 1 endoscope treatment tool
2, 23 sheath member
4 manipulating wire (wire)
5 basket portion (distal-end treating portion)
6 metal coil
7, 7a, 7b resin tube
8 distal-end member
10 protrusion
11 depression
14 elastic wires
27 high-frequency snare (distal-end treating portion)
30 endoscope
32 gripping forceps (distal-end treating portion)

The invention claimed is:

1. An endoscope treatment tool comprising:
a tubular sheath member that can be inserted into a channel of an endoscope;
a wire that is inserted into an interior of the sheath member in such a manner that the wire can be advanced/retracted in a longitudinal direction of the sheath member; and
a basket that is provided at a distal end of the wire, the basket being formed to protrude from and to be pulled into a distal-end opening in the sheath member by advancing and retracting the wire, the basket comprising a plurality of elastic wires bundled into a basket shape, the plurality of wires being expanded in a state in which the basket is made to protrude from the sheath member and being contracted by being pulled into the sheath member,
wherein the sheath member is configured having a two-layer structure in which a metal coil and a resin tube are layered in a radial direction and secured to each other at least at both end parts in the longitudinal direction thereof,
in the metal coil, lateral cross-sectional shapes of portions of a strand that are adjacent to each other in the longitudinal direction have a complementary depression and protrusion that are brought into tight contact with each other,
the resin tube has a flexural rigidity that is greater than that of the metal coil, and
the strand of the metal coil has a lateral cross-sectional shape in which at least a part of the protrusion on one side in the longitudinal direction is arc shaped and at least a part of the depression on the other side thereof is arc shaped.

2. An endoscope treatment tool according to claim 1, wherein the resin tube is disposed on an inner circumferential side of the metal coil.

3. An endoscope treatment tool according to claim 2, wherein
a thickness of the metal coil in a radial direction and a thickness of the resin tube in a radial direction have a relationship described below:

$$t1 < t2,$$

where t1 is the thickness of the metal coil in the radial direction, and t2 is the thickness of the resin tube in the radial direction.

4. An endoscope treatment tool according to claim 1, wherein a thickness of the metal coil in a radial direction and a thickness of the resin tube in a radial direction have a relationship described below:

$$t1 < t2,$$

where t1 is the thickness of the metal coil in the radial direction, and t2 is the thickness of the resin tube in the radial direction.

5. An endo scope treatment tool according to claim 1, wherein the resin tube is disposed on an outer circumferential side of the metal coil.

6. An endoscope treatment tool according to claim 5, wherein the sheath member is provided with, at a distal end thereof in the longitudinal direction, a cylindrical distal-end member that secures at least the metal coil and that has substantially the same inner diameter as that of the metal coil, and
wherein a thickness of the metal coil in a radial direction, a thickness of the resin tube in a radial direction, and a thickness of the distal-end member in a radial direction have a relationship described below:

$$t3 > t1 + t2,$$

where t1 is the thickness of the metal coil in the radial direction, t2 is the thickness of the resin tube in the radial direction, and t3 is the thickness of the distal-end member in the radial direction.

7. An endoscope treatment tool according to claim 1, wherein the metal coil and the resin tube are secured to each other at the both end parts so that surface contact between the depression and the protrusion is maintained.

8. An endoscope treatment tool according to claim 7, wherein
a thickness of the metal coil in a radial direction and a thickness of the resin tube in a radial direction have a relationship described below:

$$t1 < t2,$$

where t1 is the thickness of the metal coil in the radial direction, and t2 is the thickness of the resin tube in the radial direction.

* * * * *